United States Patent [19]

Yoshino et al.

[11] Patent Number: 4,711,541
[45] Date of Patent: Dec. 8, 1987

[54] SLIT LAMP AND ACCESSORY DEVICE THEREOF

[75] Inventors: Hisakazu Yoshino, Tokyo; Shinichi Nishimura, Ageo; Kazuyuki Sasaki, Kanazawa, all of Japan

[73] Assignee: Tokyo Kogaku Kikai Kabushiki Kaisha, Tokyo, Japan

[21] Appl. No.: 695,900

[22] Filed: Jan. 29, 1985

[30] Foreign Application Priority Data

Feb. 2, 1984 [JP] Japan .................................. 59-17569
Aug. 10, 1984 [JP] Japan ................................ 59-167664

[51] Int. Cl.⁴ ........................... A61B 3/14; A61B 3/10
[52] U.S. Cl. .................................... 351/214; 351/206
[58] Field of Search ............... 351/214, 206, 208, 221

[56] References Cited

U.S. PATENT DOCUMENTS 4,331,392 5/1982 Sato ...................................... 351/214
4,468,104 8/1984 Nunokawa ........................... 351/208

FOREIGN PATENT DOCUMENTS 52-18511 9/1978 Japan .

OTHER PUBLICATIONS

Rinsho Ganka, "Retro-Illumination Photography of Cataractous Lens", vol. 32, No. 6 (Jun. 1978), pp. 973-976.
Nippon Ganka Gakkai Zasshi (Japan Opthalologic Institute Journal), vol. 62, No. 4, 4/10/58, pp. 22-(380)-26(384).

Primary Examiner—John K. Corbin
Assistant Examiner—P. M. Dzierzynski
Attorney, Agent, or Firm—Brumbaugh, Graves, Donohue & Raymond

[57] ABSTRACT

A slit lamp comprising a slit light projection optical system having a slit aperture for projecting a slit pattern light along a slit plane to a crystalline lens of a patient's eye and a microscope for observing a section of the crystalline lens which is illuminated by the slit pattern light. The microscope comprises an crystalline lens section recording optical system including a recording device having an image plane for recording the section of the crystalline lens of the patient's eye illuminated by the slit pattern light, and a retroillumination image recording optical system for guiding a retroillumination image of the crystalline lens to the recording device of the crystalline lens section recording optical system for recording the section of the crystalline lens. The crystalline lens section recording optical system including an imaging optical system having a principal plane which intersects an extension of the image plane of the recording device in an extension plan including the slit aperture and the projection optical axis of the slit light projection optical.

14 Claims, 12 Drawing Figures

SLIT LAMP AND ACCESSORY DEVICE THEREOF

BACKGROUND OF THE INVENTION

1. Field of the Invention

The present invention relates to a slit lamp and an attachment dismountably attached to a slit lamp to make possible observation and recording of a section of the crystalline lens of a patient's eye.

2. Descriptions of Prior Art

A slit lamp is a device for projecting a slit pattern light to the crystalline lens of a patient's eye and observing and recording the projected portion. In one mode of observation, an optical sectional image is observed by viewing the crystalline lens of the patient's eye in a direction oblique to the slit projection plane. When this method is carried out with an ordinary optical system, it is impossible to obtain a satisfactorily focused image throughout the entire optical section of the crystalline lens. It has been known that the entire optical sectional image of the crystalline lens can be observed in the well-focussed state with an optical system having an image plane containing the intersecting line between the slit plane including the slit pattern light projected to the eye ball and the principal plane of the imaging optical system in the observation optical system. An apparatus for observing the section of the crystalline lens by utilizing this principle is disclosed, for example, in Japanese patent application No. 52-18511. This known apparatus is used exclusively for observation of the section of the crystalline lens, and the apparatus cannot be used as a slit lamp for other observation methods. This known apparatus is advantageous in that the entire optical sectional image of the crystalline lens formed by the slit projection light can be observed in the well-focused state. However, since one observation is limited to one section, a long time is required for observing the patient's eye entirely and discomfortable feeling is given to the patient. Furthermore, the apparatus is not provided with means for recording the position where the slit light projection is made in patient's eye. Accordingly, in case of examination of, for example, cataract, the apparatus is not suitable for precisely judging the position of the nebula and observing and recording the progress of disease.

As means for observing the entire image of the crystalline lens, there is known a retroillumination method in which a slit light is projected to patient's eye and the crystalline lens is illuminated with the slit projection light reflected from the eye fundus. It also is known that in order to prevent inclusion of a harmful cornea-reflected light into the observation optical system when observation is carried out according to this retroillumination method, a polarizer is arranged in the illumination system and an analyzer is arranged in the observation system. For example, this arrangement is disclosed in Japanese Publications "Clinical Ophthalmology", Volume 32, No. 6 (June 1978) and "Acta Societatis Ophthalmologicae Japoncae", Volume 62, 1958, Page 380. However, in the conventional apparatus utilizing the retroillumination method, uniformity of the direction of the illumination by the slit pattern light, uniformity of the quantity of the illumination light, direction and uniformity of the observation direction are not guaranteed, and the apparatus is not suitable for recording and measurement.

OBJECTS OF THE INVENTION

It is a primary object of the present invention to provide a slit lamp in which recording of the section of the crystalline lens of patient's eye and recording of the entire crystalline lens according to that retroillumination method are possible without giving any adverse influence on other functions of the slit lamp.

Another object of the present invention is to provide an accessory device for a slit lamp, which is dismountably attached to the slit lamp to effect recording of the sectional image of the crystalline lens of patient's eye and recording of the entire crystalline lens according to the retroillumination method.

SUMMARY OF THE INVENTION

According to the present invention, the above and other objects can be attained by the following structure. More specifically, in accordance with the present invention, there is provided a slit lamp comprising a slit light projection optical system for projecting a slit pattern light along a slit plane to a crystalline lens of a patient's eye and microscope means for observing a section of the crystalline lens which is illuminated by the slit pattern light, said microscope means comprising a crystalline lens section recording optical system including recording means having an image plane for recording the section of the crystalline lens of the patient's eye illuminated by the slit pattern light, and a retroillumination image recording optical system for guiding a retroillumination image of the crystalline lens to the recording means of said crystalline lens section recording optical system for recording the section of the crystalline lens, said crystalline lens section recording optical system including an imaging optical system having a principal plane which intersects an extension of the image plane of said recording means in an extension of the slit plane of the slit light projection optical system. In the present invention, the crystalline lens section recording optical system may be provided separately from an ordinary observation optical system of the slit lamp. For example, in the case where the microscope means has an observation optical system such as a binocular microscope, the crystalline lens section recording optical system may be provided separately from this observation optical system. In case where a Galilean binocular microscope is provided in the microscope means, the retroillumination image recording optical system may be constructed in such a manner that a beam splitter is located in a parallel optical flux path of one observation optical system of the binocular microscope and a reflected optical flux of the beam splitter is focussed on the recording means.

Furthermore, in the present invention, the optical system for recording the section of the crystalline lens and the optical system for recording the retroillumination image may be constructed as an attachment that can be dismountably attached to a slit lamp. This attachment is applicable to a slit lamp in which the microscope means is divided into an objective portion and an ocular portion and is inserted between the objective portion and ocular portion.

According to the present invention, since in the microscope means of the slit lamp there are disposed the optical system for recording the section of the crystalline lens, which has an optical arrangement described above, and means for guiding a retroillumination image flux of the crystalline lens to the recording means of this optical system for recording the section of the crystalline lens, a sharp image can be obtained over the entire section of the crystalline lens and simultaneously, also an entire image according to the retroillumination method can be recorded in the same recording means. Furthermore, where the optical system for recording the section of the crystalline lens is provided separately from an ordinary observation system of a slit lamp, a simultaneous recording of a sharp image of the section of the crystalline lens and a retroillumination image can be taken without any adverse influences on the inherent functions of the slit lamp. Moreover, if the optical system for recording the section of the crystalline lens and the retroillumination image recording optical system are constructed as an accessory device that can be dismountably attached to a slit lamp, it becomes possible to impart a function of simultaneous recording of an image of the section of the crystalline lens and retroillumination image to an ordinary slit lamp.

DESCRIPTION OF THE PREFERRED EMBODIMENT

First Embodiment

Figure 1:
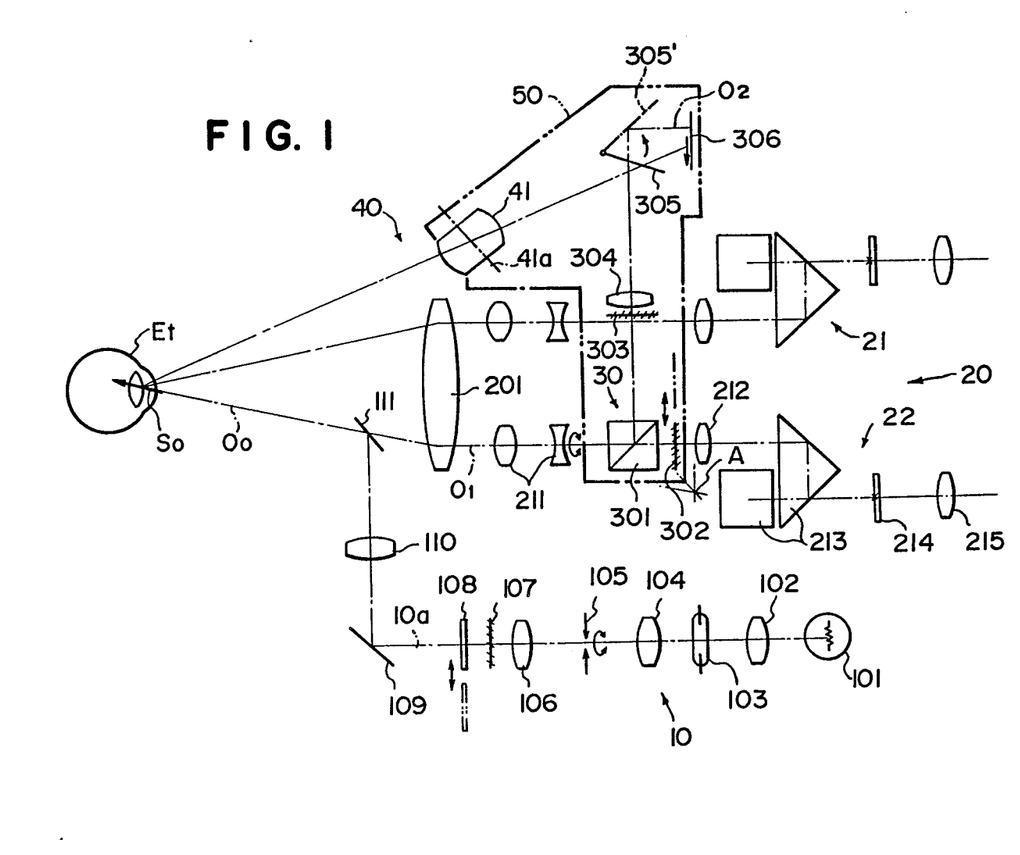
FIGS. 1, 2 and 3 are schematic diagrams illustrating the optical systems of different embodiments of the present invention.

General Structure:

Referring to FIG. 1, a slit lamp shown in the drawings has a slit projection optical system 10 and a microscope 20 for observing patient's eye. A housing 50 is dismountably attached to the body portion of the slit lamp, and a retroillumination image recording optical system 30 and an optical system 40 for recording the section of the crystalline lens are arranged within the housing 50.

Slit Projection Optial System 10:

The slit projection optical system 10 has an observation tungsten lamp 101 and a photographing xenon lamp 103 as light sources, and a condenser 102 is arranged between the tungsten lamp 101 and the xenon lamp 103. Furthermore, another condenser 104 is arranged to guide a light flux from the light source along a projection light path 10a, and a slit aperture 105 is arranged in the projection light path 10a. The slit aperture 105 is disposed to transmit the light flux from the light source in the form of a fine slit, and the slit light flux which has passed through this slit aperture 105, passes through a first objective lens 106 and is reflected at right angle by a mirror 109, and the slit light flux then passes through a second objective lens 110 and is reflected from a half mirror 111. Then, the slit light flux is projected in a direction of the projection optical axis Oo to patient's eye Et. The slit aperture 105 is rotatable around the slit projection optical path 10a as indicated by an arrow and can optionally change the direction of the projection slit. A polarizer 107 and a filter 108, if necessary, are retractably arranged in the projection light path 10a.

The condenser 102 focusses a filament image of the tungsten lamp 101 on the electrode spacing, that is, the light-emitting point, of the xenon lamp 103, and the condenser 104 converts the light from these light sources to a parallel light flux. The first objective lens 106 has a front focal point at the position of the slit aperture 105 and converts the light flux, which has passed through the slit aperture 105, to a parallel light flux. The second objective lens 110 focusses the light flux, which has passed through the first objective lens 106, on the anterior portion of patient's eye Et, mainly the crystalline lens, as a slit image So. As is well-known with respect to an ordinary slit lamp, it is preferred that the slit length and slit width of the slit aperture 105 be optionally adjustable. It also is preferred that various plates having a circular opening and differing in the opening diameter be arranged in close proximity to the slit aperture 105 so that a circular spot light having an optimal size can be projected to the anterior portion of patient's eye.

Microscope 20:

This microscope 20 consists of a Galilean binocular microscope having an observation optical system 21 for the right eye and an observation optical system 22 for the left eye. Both the observation optical systems 21 and 22 have an objective lens 201 in common, and variable-power lenses 211 for the optical systems 21 and 22 are arranged in parallel to each other in the rear of the objective lens 201 to construct an objective zone. A variable-power lens of the rotary drum type or other known type can be used as the variable-power lens 211. The ocular zone of the observation optical systems 21 to 22 has an image formation lens 212 arranged on the optical axis $0_1$ of the variable-power lens 211, an erect prism 213 arranged in the rear of the image formation lens 212 and an image plate 214 arranged on the outgoing side of the erect prism 213. The objective lens 201 is arranged so that the light which has advances along the spot projection light axis Oo from patient's eye Et and has passed through the half mirror 111 advances along the optical axis $0_1$ of the variable-power lens 211 of the left observation optical system 22. After passage through the variable-power lens 211, this light flux is focussed on the image plate 214 by the imaging lens 212. An image formed on the image plate 214 is observed through an ocular lens 215. The image of the crystalline lens of patient's eye can also be observed through the observation optical system 21 for the right eye having an arrangement symmetric with the observation optical system 22 for the left eye, and stereoscopic observation of the crystalline lens of patient's eye can be performed by the optical systems 21 and 22 for the right and left eyes.

Retroillumination Image Observing and Recording Optical System 30:

This optical system has a beam splitter 301 inserted between the variable-power lens 211 and image formation lens 212 of the observation optical system 22 for the left eye. This beam splitter 301 reflects a part of the light flux which has passed through the variable-power lens 211 and transmits the remainder as it is. In the transmission light path of the beam splitter 301, an analyzer 302 having a polarization axis rectangular to the polarization axis of the polarizer 107 of the slit projection optical system 10 is retractably arranged as indicated by an arrow. By this analyzer 302, the light reflected from the surface of the cornea of patient's eye can be protected from intruding into the ocular portion of the optical system 22.

An analyzer 303 similar to the analyser 302 and a condenser 304 are arranged on a reflection optical path of the beam splitter 301. The light which has passed through the condenser 304 is reflected to a photographing film 306 when a spring-up mirror 305 of the optical system 40 for recording the section of the crystalline lens, described hereinafter, is located at a spring-up position 305' indicated by an ideal line in the drawings, and a retroillumination image is focussed on the film 306.

Optical System 40 for Recording Section of Crystalline Lens:

This optical system 40 comprises a photographing lens 41, and the above-mentioned spring-up mirror 305 and photographing film 306. The photographing lens 41 and photographing film 306 have an optical arrangement according to the principle of Scheimpflug with respect to the plane including the slit image So in patient's eye Et, that is, the slit projection plane. More specifically, the slit projection plane intersects the plane including the film 306 at a point A shown in FIG. 1, and the plane including the principal plane 41a of the photographing lens 41 includes the intersecting line between the slit projection plane and the plane of the film. By adoption of this arrangement, the entire slit image So can be formed on the photographing film 306 in the well-focussed state.

Structure of Accessory Device of Slit Lamp:

The respective parts constituting the above-mentioned retroillumination image observing and recording optical system 30 and the above-mentioned optical system 40 for recording the section of the crystalline lens are contained in the housing 50. The housing 50 is mounted on the body portion of the slit lamp so that the housing can be rotated within a range of 180° around the optical axis $0_1$ of the left eye observation optical system of the microscope zone 20.

Operation:

(1) Projection for observation of retroillumination image

A slit light is projected on the crystalline lens from the slit projection optical system 10. The analyzer 302 of the retroillumination image observation system is retreated from the optical path, and the slit projection position is aligned by moving the whole apparatus in both the vertical and horizontal directions while examining the reflection of the slit light from the cornea.

The slit light projected to the crystalline lens is reflected on the eye fundus and the crystalline lens is illuminated from the back with this reflected light.

The retroillumination image of the crystalline lens is observed through the retroillumination image observing optical system. At this point, in order to prevent the light reflected from the cornea from having had influences on the observation of the retroillumination image, the analyzer 302 is inserted into the optical path. Since the polarization axis of this analyzer 302 intersects the polarization axis of the polarizer 107 of the projection optical system 10 at a right angle, the light reflected from the eye fundus is intercepted. The eye fundus may be regarded as being equivalent to a diffusing surface and the reflection of the retroillumination image-forming slit light from the eye fundus is a non-polarized light having no substantial polarizing property. Accordingly, the retroillumination image passes through the analyzer 302 and is focussed on the image plate 214 by the image forming lens 212, and the retroillumination image is observed through the ocular lens 215.

Photographing is performed according to the following procedures. By instructions of a release (not shown), the spring-up mirror 305 is sprung up to the spring-up position 305' and a light is emitted from the xenon lamp 103. The retroillumination image is partially reflected by the beam splitter 301 and the light reflected from the cornea is intercepted by the analyser 303, and the retroillumination image is photographed on the film 306 through the spring-up mirror 305 by the photographing lens 304. Incidentally, focussing of the retroillumination image is accomplished by moving the entire apparatus in the horizontal direction.

(2) Photographing of section of crystalline lens

Figure 7:
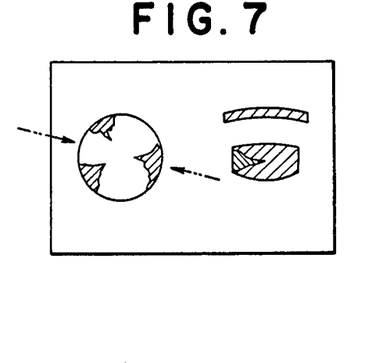
FIGS. 7 and 8 are diagrams showing examples of the photographed images.

The photographing optical path is opened by springing up the spring-up mirror 305, and simultaneously, a light is emitted from the xenon lamp 103 and the image of the section of the crystalline lens is photographed on the film 306 as well as the retroillumination image. An example of the projection for this photographing is illustrated in FIG. 7.

In the case where a sectional image on other longitude has been photographed, the slit aperture 105 of the slit projection optical system 10 is rotated around the projection optical axis. If the analyzer 302 of the retroillumination image observing optical system is retreated from the optical path, the direction of the incident longitude of the slit can be observed by the light reflected from the cornea. Accordingly, the direction of the incident longitude of the slit can be aligned at a desired position, and the angle of the longitude can be known from an indicator (not shown) linked with the slit aperture 105 and a scale (not shown). By utilizing a scale and indicator (not shown) attached to the housing 50, the housing 50 is rotated around the optical axis 01 so that the same angle as the angle of the longitude is indicated.

Second Embodiment

Figure 2:
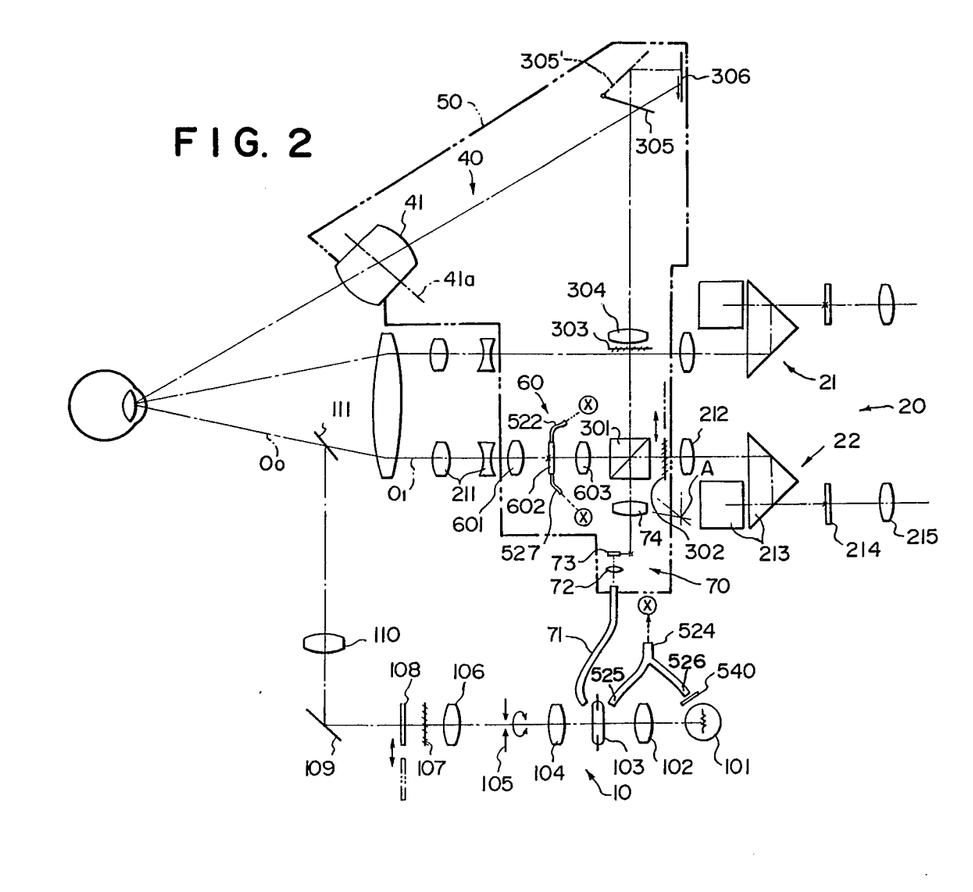

This embodiment is to record the slit projection direction on the film 306, and an optical system 60 for observing and recording the projection direction is further disposed. This optical system 60 comprises an image forming lens 601, a freely rotatably, light-emitting focussing plate, that is, a reticle 602, and a relay lens 603. The image forming lens 601 is disposed to focus a retroillumination image on the reticle 602, and the relay lens 603 is disposed to guide the flux from the image on the reticle 602 to the beam splitter 301 again in the form of parallel fluxes.

Figures 5, 6:
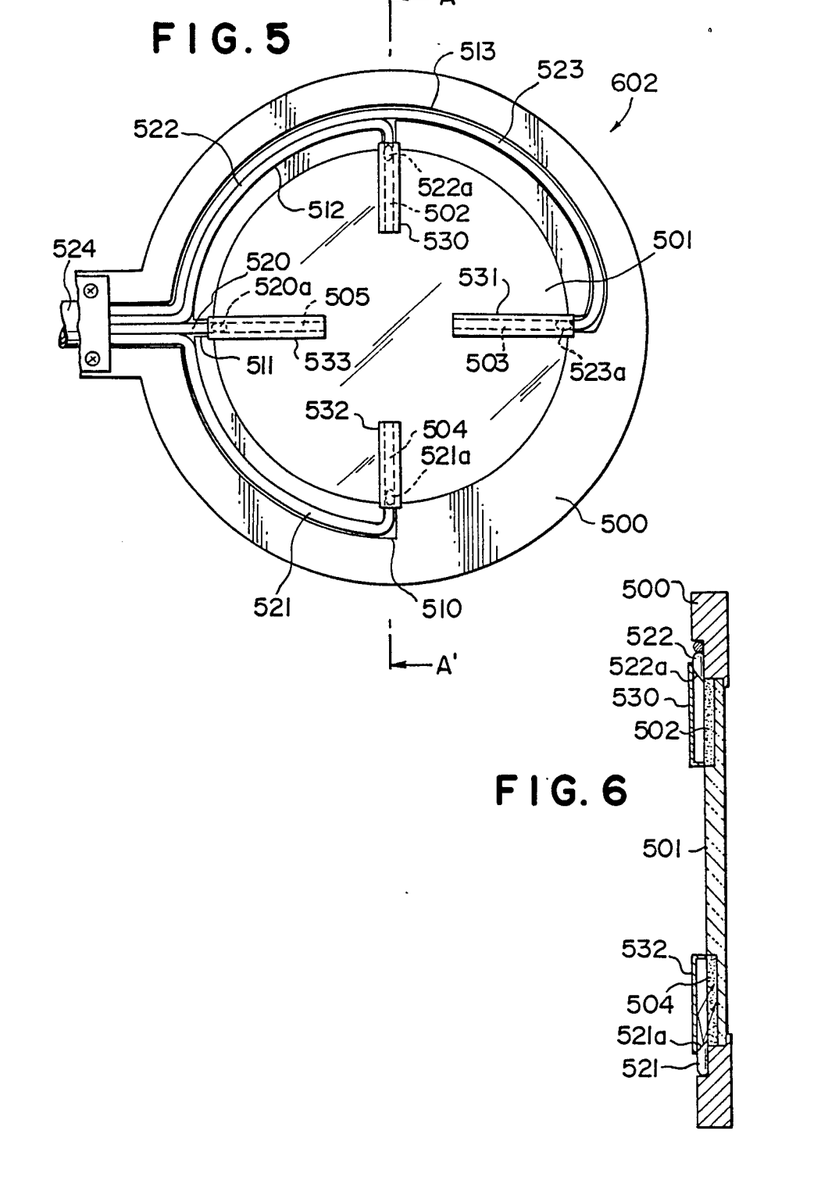
FIG. 5 is a front view showing a reticle arranged in the photographing optical system for the retroillumination method.
FIG. 6 is a view showing the section of the reticle of FIG. 5 taken along the line A—A.

As shown in FIGS. 5 and 6, the reticle 602 comprises a holding frame 500 and a transparent glass plate 501 fitted and bonded to the holding frame 500, and line grooves 502, 503, 504 and 505 are formed on the glass plate 501 at intervals of 90° in the circumferential direction. Semi-circular tubes 530, 531, 532 and 533, each having a light-reflecting inner wall, are bonded to the line grooves 502 through 505, respectively.

Grooves 510, 511, 512 and 513 are formed on the holding frame 500 along the circumferential direction, and optical fibers 520, 521, 522 and 523 are fitted and bonded into these grooves 510 through 513, respectively. Emission ends 520a, 521a, 522a and 523a of these optical fibers are obliquely cut, and the optical fibers are arranged so that the obliquely cut sections are located above at the ends of the above-mentioned grooves. The four optical fibers 520 through 523 are gathered into one fiber bundle 524, and the fiber bundle 524 is laid out in the projection optical system 10 and is divided into two branches in the midway. One incident end 525 is arranged to confront the xenon lamp 103 and the other incident end 526 is arranged to confront the tungsten lamp 101. A monochromatic filter 540 of, for example, a green color is arranged between the incident end 526 and the tungsten lamp 101.

The light from the tungsten lamp 101 is converted to a green color light by the filter 540 and is incident into the optical fibers and emitted from the emission ends. Since the emission ends have obliquely cut faces, most of the outgoing light is refracted and emitted toward the line grooves 502 through 505 of the glass plate 501, diffused on the diffusing surfaces of the groove walls, transmitted through the plate sheet 501 and emitted to the side of the relay lens 603. The light flux, which is emitted on the side opposite to the line grooves, is reflected on the reflecting inner walls of the semi-circular tubes 530 through 533 and incident on the line grooves.

In the present embodiment, there is further disposed a density chart photographing system 70. This photographing system 70 has an optical fiber 71 having one end arranged to confront the xenon lamp 103. The other end of the optical fiber 71 is arranged to confront the illuminating lens 72. A density filter 73 is arranged at the back of the illuminating lens 72, and information on the density filter 73 is photographed on the film 306 through the retroillumination image recording system 30 by a photographing lens 74. The density filter 73 is arranged eccentrically with respect to the photographing lens 74.

Figure 4A:
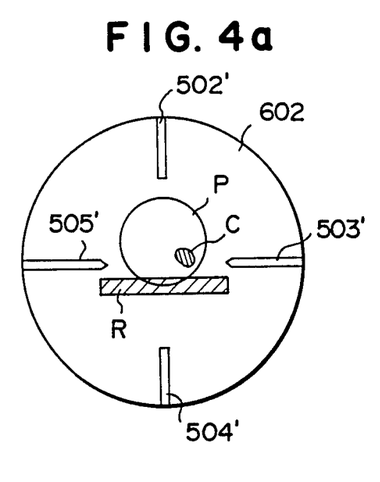
FIGS. 4a, 4b, 4c and 4d are diagrams showing images on the ocular.
Figure 4B:
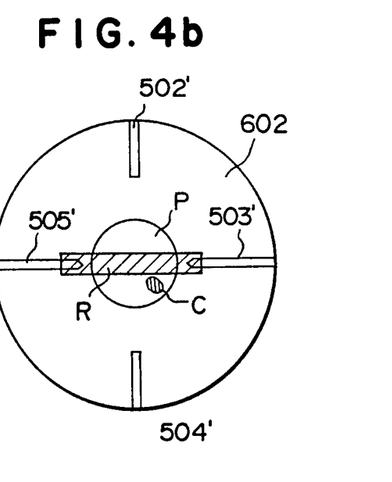

Operation:

The analyzer 302 is retreated from the optical path, and the observation light source 101 of the projection optical system 10 is lighted to project the slit light from the slit 105 to patient's eye. The light from the light source 101 passes through the green filter 540 and the optical fiber 524 and illuminates the engraved lines 502 through 505 of the reticle 602, and an inspector can observe a green image of the crossing lines 502' through 505' in the visual field of the ocular lens, as shown in FIGS. 4a, 4b, 4c and 4d. If the alignment of patient's eye with the apparatus is not complete, as shown in FIG. 4a, the center of the pupil P of patient's eye is not in agreement with the center of the image R formed by partial reflection of the slit light on the cornea of patient's eye and these centers are not in agreement with the crossing center of the image of the crossing lines 502' through 505'. The center of the pupil P is made in agreement with the crossing center of the slit image by appropriately moving the slit lamp proper in both the vertical and horizontal directions, so that alignment is established between the slit image R and the horizonatal slit images 503' and 505' (see FIG. 4b).

Figure 4C:
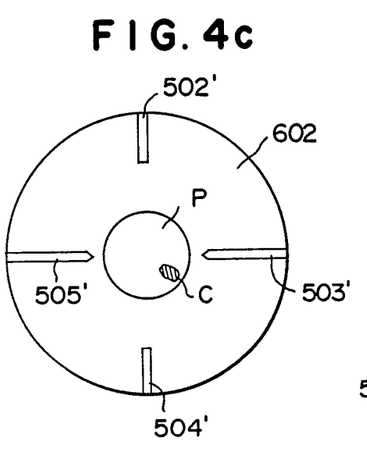

Then, the analyzer 302 is inserted in the optical path. Since the polarization axis of the slit image R formed by the slit light reflected from the cornea is rectangular to the polarization axis of the polarizer 107, the slit image R is intercepted by the analyzer 302 (see FIG. 4c). On the other hand, the reflection of the slit light from the eye fundus is converted to a non-polarized light flux having no substantial polarizing property by the diffusing action of the eye fundus, and a retroillumination image of patient's eye is formed by illumination with this reflected light. Accordingly, the inspector can observe the retroillumination image by the light flux not intercepted by the analyzer 302, and this observation is not influenced by the light reflected from the cornea at all. Focussing of the retroillumination image can be accomplished by the horizontal movement of the slit lamp proper.

Figure 4D:
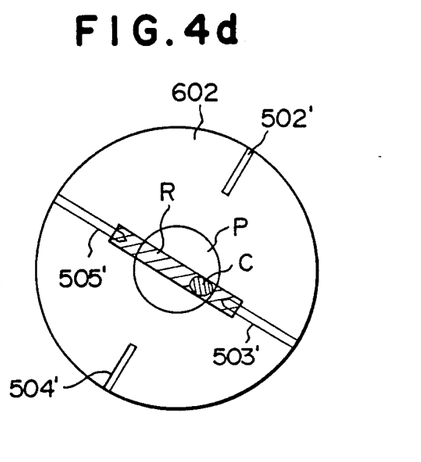

The analyzer 302 is retreated from the optical path again, and the slit aperture 105 and housing 50 are rotated, whereby the image R of the reflection of the slit light from the cornea and the horizontal slit images 503' and 505' aligned therewith are moved to a desired longitude position (see FIG. 4d).

Figure 8:
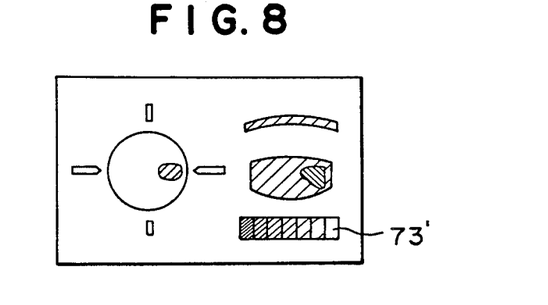

By operating a release switch for photographing (not shown), the spring-up mirror 305 is sprung up, and simultaneously, the xenon lamp 103 is lighted. By springing-up of the spring-up mirror 305, the optical path for photographing the section of the crystalline lens is opened and as shown in FIG. 8, the image of the section is photographed on the film 306. Simultaneously, the retroillumination image, as well as the crossing line image of reticule 602, is reflected at the spring-up position of the spring-up mirror 305 and photographed on the film 306.

Third Embodiment

Figure 3:
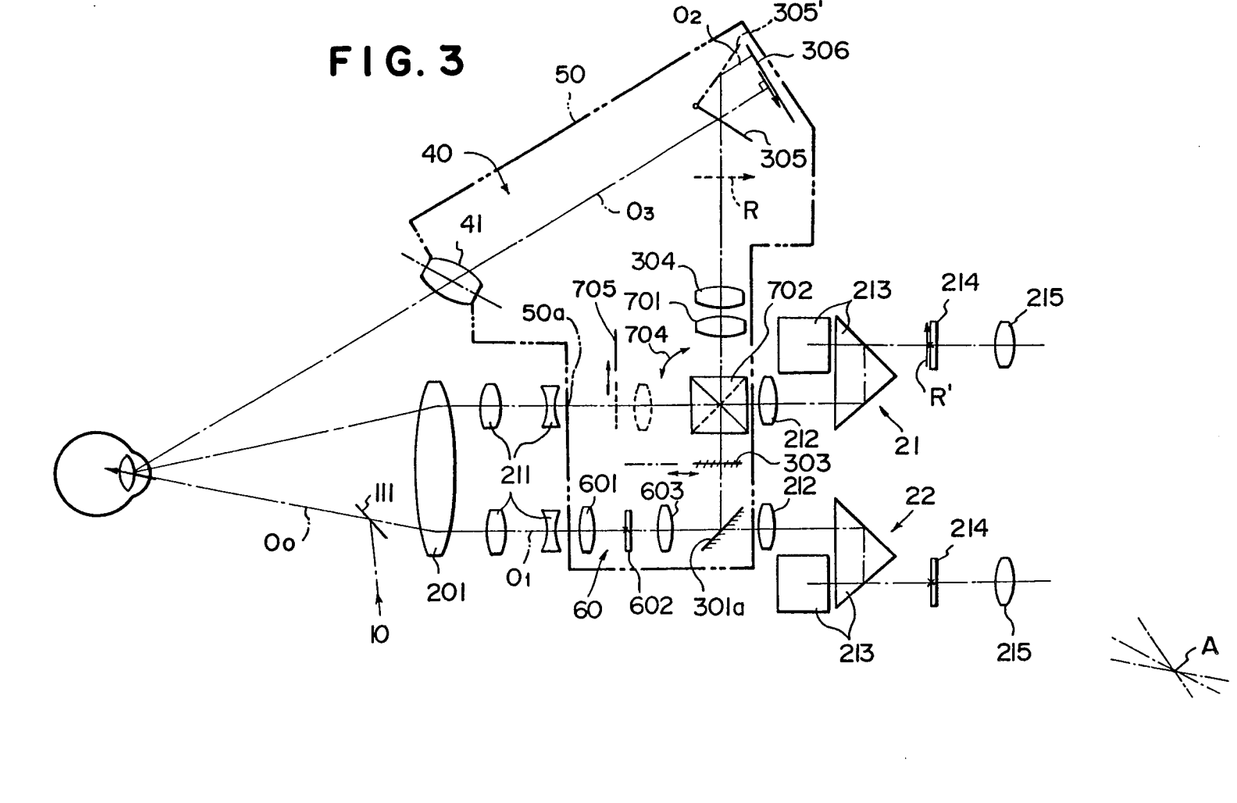

According to this embodiment, observation of the sectional image of the crystalline lens becomes possible. For this observation, a beam splitter 702 is arranged between the variable-power lens 211 and the image forming lens 212 in the observation optical system 21 for the right eye. A lens 701 is combined with this beam splitter 702, and the lens 701 can be rotated, together with the beam splitter 702, in the direction indicated by an arrow 704. When the reflecting surface of the beam splitter 702 is located at a position indicated by a solid line in the drawings, the lens 701 is placed in the optical path for photographing the retroillumination image, and when the reflecting surface of the beam splitter 702 is located at a position indicated by a dotted line, the lens 701 is arranged coaxially with the variable-power lens 211 of the observation optical system for the right eye. In the observation optical system 22 for the left eye, a mirror 301a is disposed at the position of the above-mentioned beam splitter 301 to reflect the light flux from the variable-power lens 211 toward the photographing lens 304. When the spring-up mirror 305 is located at a position indicated by a solid line in the drawings, the spring-up mirror 305 reflects the light flux from the photographing lens 41 of the optical system 40 for photographing the section of the crystalline lens in the opposite direction along the optical path for phototgraphing the retroillumination image. This light flux forms an intermediate image at the position R.

Figure 9:
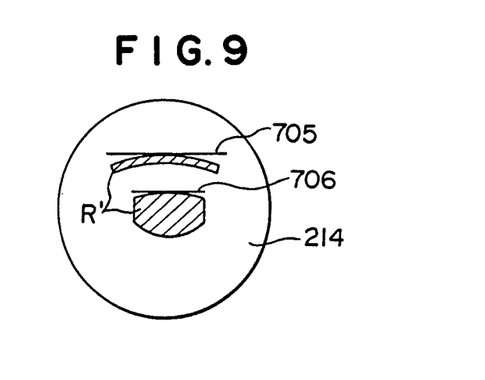
FIG. 9 is a diagram showing a reticle of the ocular in the third embodiment.

The light flux from the intermediate image R is converted to parallel fluxes by co-operation of the photographing lens 304 of the system for photographing the retroillumination image and the lens 701, reflected on the reflecting surface of the beam splitter 702 located at the position indicated by a solid line and made incident on the image forming lens 212 to form an image R' corresponding to the intermediate image R on the reticle 214. As shown in FIG. 9, the reticle 214 has indicator lines 705 and 706, and the entire apparatus is moved in the horizontal direction so that the front face of the section of the cornea and the front face of the section of the crystalline lens are located on these indicator lines. If this alignment is performed, the focussing positions for observation of the retroillumination image and for photographing can be kept constant and the reproducibility can be enhanced.

As the step of observing the retroillumination image, the beam splitter 702 and lens 701 are turned to the position indicated by a dotted line. At this position, the light flux which has passed through the variable-power lens 211 of the observation optical system 22 for the left eye is reflected by the mirror 301a and then by the reflecting surface of the beam splitter 702 and the flux of the retroilluminating image is guided to the image forming lens 212 of the observation optical system 21 for the right eye.

At the photographing step, when the spring-up mirror 305 is sprung up, the flux of the retroillumination image reflected from the mirror 301a is focussed on the film 306 through the mirror 305' at the spring-up position by means of the lens 304 to form a retroillumination image. At this time, the light flux which has passed through the variable-power lens 211 of the observation optical system 21 for the right eye is reflected from the reflecting surface of the beam splitter 702, entering into the retroillumination image photographing system may be intercepted by the wall face 50a of the housing 50 or by a shutter 705 linked with the spring-up mirror 305, which is arranged between the lens 211 and the beam splitter 702. If the housing 50 is dismounted from the body portion of the slit lamp, this slit lamp can be used as an ordinary slit lamp having a binocular microscope.

The invention has thus been shown and described with reference to specific embodiments, however, it should be noted that the invention is in no way limited to the details of the illustrated structures but changes and modifications may be made without departing from the scope of the appended claim.

What is claimed is:

1. A slit lamp comprising:
    a slit light projection optical system including a projection lens and a slit aperture for projecting a light flux to a fundus via a crystalline lens of a patient's eye, and first polarizing means for polarizing said light flux, said projection lens forming an image of said slit aperture onto the crystalline lens so as to cut optically the crystalline lens for forming an optical section thereof;
    microscope means, having an objective lens, for observing the optical section of the crystalline lens;
    a first recording optical system including a photographing lens and recording means, said photographing lens having a principal plane which intersects an extension of an image plane on said recording means of said first recording optical system in an extension of a slit projection plane, said photographing lens forming an image of the optical section of the crystalline lens onto said recording means; and
    a second recording optical system, being composed of said objective lens of said microscope means, light deflection means, analyzing means having a polarization axis rectangular to that of the first polarizing means, and an imaging lens, for guiding and imaging on the recording means of said first recording optical system a retroillumination image of the crystalline lens resulting from illumination of the lens from the back by the light flux reflected at the fundus of the patient's eye.

2. The slit lamp as set forth in claim 1, wherein said recording means of said first recording optical system is a photographic film.

3. The slit lamp as set forth in claim 1, wherein said slit aperture of said slit light projection optical system is rotatable about a projection optical axis, said first recording optical system and said light deflection means and said imaging lens of said second recording optical system being rotatable as a unit about an optical axis of an observation optical system of said microscope means.

4. The slit lamp as set forth in claim 1 further comprising:
    an optical system for observing and recording on said recording means of said first optical recording system the slit projection direction including a rotatable reticle having cross lines thereon and optical fiber means for illuminating said cross lines,
    an image forming lens for focusing said retroillumination image onto said reticle
    a relay lens for guiding the light flux from the reticle, including said retroillumination image and an image of said cross lines, to said light deflection means of said second recording optical system.

5. The slit lamp as set forth in claim 1, wherein said microscope means comprises a Galilean type binocular microscope, and said light deflection means is a beam splitter arranged in a parallel optical path of one observation optical system of said binocular microscope.

6. The slit lamp as set forth in claim 5, wherein said beam splitter is rotatably aligned with a lens, said lens being placed to guide the retroillumination image to said recording means when said beam splitter is rotated to a first position, and said lens being placed to guide the optical image of the crystalline lens section and an image of a section of the cornea to a reticle provided in said microscope means, for focusing and observing said images, when said beam splitter is rotated to a second position.

7. The slit lamp as set forth in claim 5, wherein said observation optical system includes an optical path through said beam splitter including second analyzing means having a polarization axis rectangular to that of the first polarizing means and being retractably arranged in a transmission optical path of said beam splitter.

8. An accessory device for use in combination with a slit lamp, said slit lamp comprising a slit light projection optical system including a projection lens, a slit aperture, and polarizing means for polarizing a light flux, said projection lens projecting said light flux to a fundus via a crystalline lens of a patient's eye, said projecting lens forming an image of said slit aperture onto the crystalline lens so as to cut optically the crystalline lens for making an optical section thereof, microscope means for observing the optical section of the crystalline lens, and said microscope means being able to be divided into an objective portion having an objective lens and an ocular portion having observation means, said objective portion having means for receiving an attachment portion of said accessory device;
    said accessory device having an attachment portion with attachment means for dismountably attaching said accessory device onto said objective portion of said microscope means;
    said accessory device comprising:
        a first recording optical system including a photographing lens and recording means, said photographing lens of said first recording optical system having a principal plane which intersects an extension of an image plane on said recording means in an extension of a slit projection plane including an axis of the slit image in the patient's eye, said photographing lens forming an image of the optical section of the crystalline lens onto said recording means, and a second recording optical system being composed of light deflection means, an imaging lens and analyzing means having a polarization axis rectangular to that of said polarizing means in optical alignment with said objective lens of said objective portion of said microscope means, for guiding and imaging on the recording means of said first recording optical system, a retroillumination image of the crystalline lens resulting from illumination of the lens from the back by the light flux reflected at the fundus of the patient's eye, when said accessory device is attached onto said objective portion of said microscope means.

9. The accessory device as set forth in claim 8, wherein said recording means of said first recording optical system is a photographic film.

10. The accessory device as set forth in claim 8, which is used with said slit lamp wherein said slit aperture is rotatable about an optical axis of the said projection lens, and rotatable about an optical axis of the objective lens of the slit lamp.

11. The accessory device as set forth in claim 8, further comprising a density chart photographing system including optical fiber means for confronting a light source of said slit light projection optical system, an illumination lens for guiding light from said optical fiber means to a density filter and a photographing lens for guiding light from said density filter onto said light deflection means of said second recording optical system for recording onto said recording means of said first optical recording system.

12. The accessory device as set forth in claim 8, wherein said microscope means is a Galilean type binocular microscope having an objective portion with two parallel optical paths and said light deflection means is arranged in one of said optical paths.

13. The accessory device as set forth in claim 8, which further comprises second attachment means for attaching dismountably said observation means of said microscope means, and wherein said light deflection means of said second recording optical system is a beam splitter, a transmission optical path of which is coaxial to an optical path of the observation means of said microscope means.

14. The accessory device as set forth in claim 13, which further includes a second analyzer retractably arranged in the transmission optical path of said beam splitter and having a polarization axis rectangular to that of the polarizer of said slit lamp.

* * * * *